United States Patent
Blasche et al.

(10) Patent No.: US 6,424,855 B1
(45) Date of Patent: Jul. 23, 2002

(54) MEDICAL DIAGNOSTIC IMAGING APPARATUS

(75) Inventors: Mathias Blasche, Buckenhof; Matthias Drobnitzky, Spardorf, both of (DE)

(73) Assignee: Siemens Aktiengesellschaft, Munich (DE)

( * ) Notice: Subject to any disclaimer, the term of this patent is extended or adjusted under 35 U.S.C. 154(b) by 5 days.

(21) Appl. No.: 09/676,651

(22) Filed: Sep. 29, 2000

(30) Foreign Application Priority Data

Oct. 1, 1999 (DE) .......................... 199 47 422

(51) Int. Cl.⁷ .............................. A61B 5/05
(52) U.S. Cl. .............. 600/425; 600/407; 600/415; 600/417; 250/491.1
(58) Field of Search ................. 600/407, 415, 600/417, 429, 425; 378/20, 205; 250/491.1; 324/318

(56) References Cited

U.S. PATENT DOCUMENTS

| | | | |
|---|---|---|---|
| 4,117,337 A | | 9/1978 | Staats |
| 4,242,587 A | * | 12/1980 | Lescrenier .................. 378/20 |
| 4,629,989 A | * | 12/1986 | Riehl et al. ................. 324/318 |
| 5,204,629 A | * | 4/1993 | Ueyama ..................... 324/318 |
| 5,309,913 A | | 5/1994 | Kormos et al. |
| 5,828,770 A | | 10/1998 | Leis et al. |
| 5,923,417 A | | 7/1999 | Leis |

FOREIGN PATENT DOCUMENTS

DE   OS 195 08 715   9/1996

* cited by examiner

Primary Examiner—Marvin M. Lateef
Assistant Examiner—Runa Shah Qaderi
(74) Attorney, Agent, or Firm—Schiff Hardin & Waite

(57) ABSTRACT

A medical diagnostic imaging device has a support device, which, for positioning a fixable area of an examination subject to be imaged in an imaging volume of the device, is fashioned for moving the examination subject thereon in at least one moving direction, a control device for controlling the movement of the support device, a pointer device, which, for prescribing the area to be imaged, is fashioned for pointing to the area to be imaged, and an detection device, acquires the spatial position of the pointer device at least in the moving direction and which is connected to the control device for positioning the area to be imaged that is prescribed by the pointer device.

17 Claims, 1 Drawing Sheet

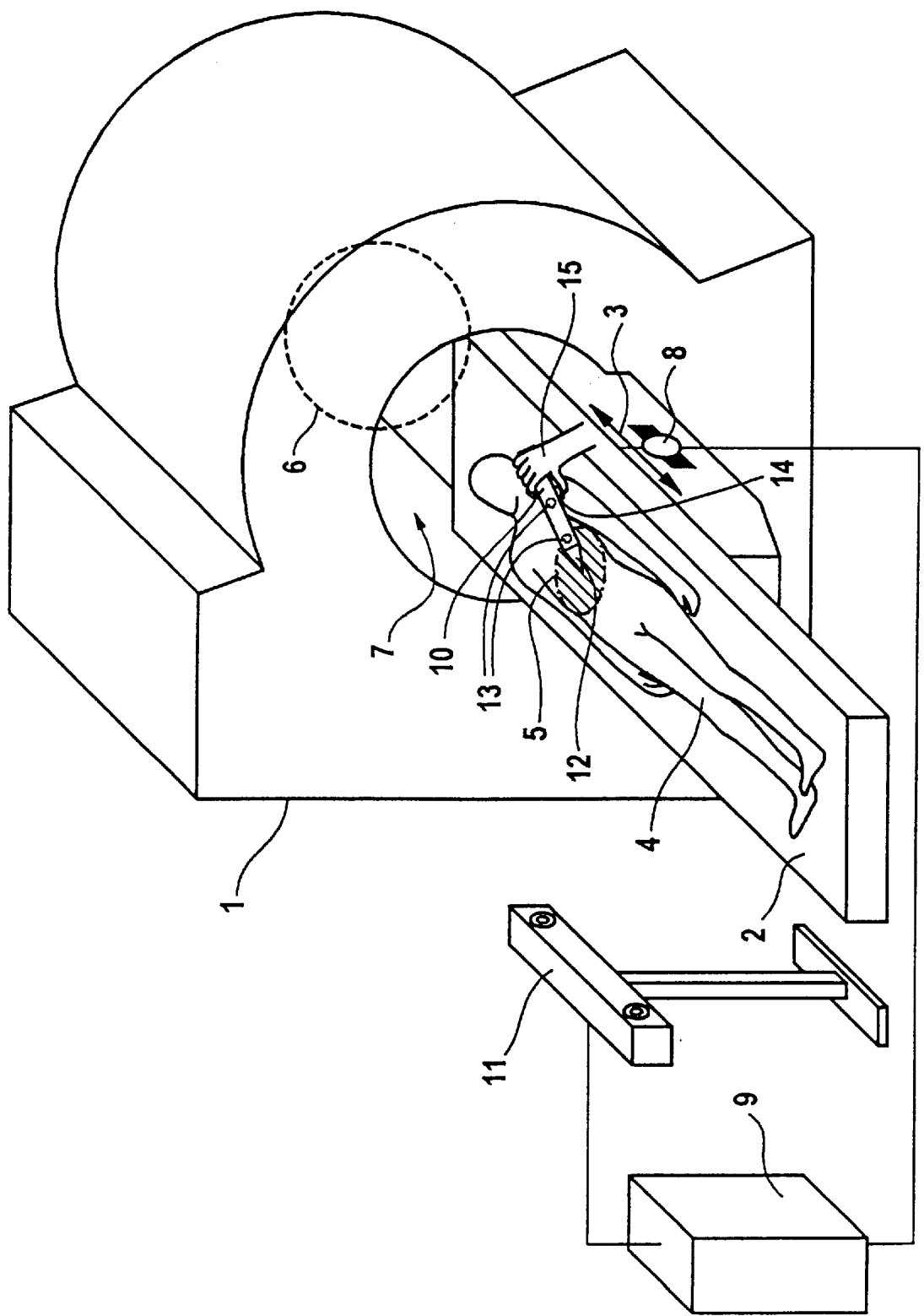

MEDICAL DIAGNOSTIC IMAGING APPARATUS

BACKGROUND OF THE INVENTION

1. Field of the Invention

The present invention relates to a medical diagnostic imaging device.

2. Description of the Prior Art

In medical diagnostic imaging devices, such as computed or magnetic resonance tomography devices, an area of an examination subject to be imaged is positioned in an imaging volume of the diagnostic device for preparing images of this area. Particularly in magnetic resonance tomography devices, wherein, apart from a pickup opening, the imaging volume is frequently surrounded by a closed housing within the examination space, the positioning ensues with the aid of a support device that can be moved in at least one direction and on which the examination subject is borne. A projector which projects an optical marker onto the examination subject can be situated in the area of the pickup opening. In an initial moving process of the support device, the support device including the patient borne thereon is initially controlled such that the optical marker marks a center of the area to be imaged on the surface of the patient. A remaining moving path of the support device in the imaging volume results from the known distance of the optical marker from the imaging volume. For fixing the center of the area to be imaged, often the support device must be moved back and forth until the optical marker meets the desired center. Since the support device also exhibits a comparatively low moving speed, the aforementioned positioning is comparatively time-consuming. U.S. Pat. No. 4,117,337 describes a comparable positioning device for a computed tomography device.

In contrast to the aforementioned positioning, German OS 195 08 715 describes a method and a device for positioning a patient in an imaging medical diagnostic device with which the positioning is more reliable and faster. For this purpose, the area to be imaged is marked with a marker fixed onto the patient. An image pickup device, such as a video camera, acquires the marker fixed onto the patient in an image outside of the examination space. An imaging processing unit recognizes the marker in the image and determines its spatial position. A control device determines the moving path of the support device from the spatial position of the marker and the known position of the imaging volume, and controls a movement of the bearing device along the aforementioned moving path.

A particular disadvantage of the aforementioned device is that a complicated and expensive system containing an image pickup device and an image processing unit with corresponding software is utilized for determining the position of the marker. Furthermore, it is possible that the marker will adhere differently as a result of different surface conditions of garments or on the skin of the patient, so that the marker may become displaced. Moreover, many patients consider attachment of the marker as being unpleasant, particularly on the face.

U.S. Pat. No. 5,309,913 discloses a support device that is independent of an image-generating medical diagnostic device, this support device including a detection device for acquiring the position of a pointer device for navigating within diagnostic image data sets, particularly for supporting a stereotactic brain operation. The diagnostic image data sets, earlier in time, are generated with a medical diagnostic imaging device.

SUMMARY OF THE INVENTION

An object of the present invention is to provide a medical diagnostic imaging device that allows fast positioning of the examination subject and reduces the aforementioned disadvantages of known devices.

This object is inventively achieved in a medical diagnostic imaging device having a support device, which, for positioning a fixable area of an examination subject to be imaged in an imaging volume of the device, is fashioned for moving the examination subject thereon in at least one moving direction, a control device, which controls the movement of the support device, a pointer device, which, for prescribing the area to be imaged, points to the area to be imaged, and a detection device, which acquires the spatial position of the pointer device at least in the moving direction and which is connected to the control device for positioning the area to be imaged that is prescribed by the pointer device.

The area to be imaged can be simply and intuitively fixed by a person who is part of the diagnostic process who touches, for example, a corresponding point of the area to be imaged at a surface of the examination subject, with the pointer device. The spatial position of the pointer device can be detected by means of the detection device. A moving path of the bearing device, for positioning the area to be imaged in the imaging volume, can be detected from the spatial position of the pointer device and from a known initial position of the support device. In an initial moving process, the aforementioned moving path is traversed without interruptions. Thus, the time-intensive positioning process described above employing of an optical projection. Furthermore, a marker need not be attached onto the examination subject for fixing the area to be imaged. Moreover, the pointer and detection device are comparatively simple and therefore can be economically fashioned compared to image pickup device having an image processing unit and corresponding image recognition software.

In an embodiment, the pointer device is fashioned so as to be free of a fixed connection to the other device. A high degree of operating comfort is achieved for the person carrying out the diagnosis, particularly in an embodiment wherein the pointer is a hand-held device that is not mechanically connected to the diagnostic device.

In another embodiment, the detection device is disposed at a known distance from a part of the imaging device that cannot be moved. It is thereby achieved that the spatial position of the pointer device detected by the detection device exhibits a fixed reference to the diagnostic device.

In another embodiment, the pointer device and the detection device are fashioned such that the detection device can detect the spatial position as well as the orientation of the pointer device. For example, a center of the area to be imaged can be fixed more accurately as a result, particularly when the center within an examination subject is to be prescribed for all three spatial directions.

In a further embodiment, the pointer device and the detection device are fashioned such that the detection device can optically detect the spatial position and, if necessary, potentially the orientation of the pointer device. For example, U.S. Pat. Nos. 5,828,770 and 5,923,417 describe an embodiment for optical detection for this purpose. Optical detection ensures a reliable detection even in an environment with severe electromagnetic interference, as is present of a magnetic resonance tomography device, for example.

For this purpose, the detection device is a stereoscopic camera in an advantageous embodiment.

In another embodiment, the medical diagnostic imaging device is a computed or magnetic resonance tomography device. Particularly computed and magnetic resonance tomography devices represent medical diagnostic devices with a considerable original cost, so that a high utilization rate (throughput) is desired for such devices. The throughput is increased by reducing the examination time per patient, for example. When the area to be imaged is fixed in a simple, intuitive and fast manner, the positioning process per patient is reduced by approximately half a minute up to a full minute, so that approximately one to two more patients can be additionally examined per day, so that the patient throughput is increased. As used herein, "computed tomography device" includes X-ray and electron beam computed tomography devices, as well as positron emission tomography devices.

DESCRIPTION OF THE DRAWINGS

The single FIGURE is a schematic block diagram of a medical diagnostic imaging apparatus constructed and operating in accordance with the principles of the present invention.

DESCRIPTION OF THE PREFERRED EMBODIMENTS

In an embodiment of the invention, the figure shows a magnetic resonance tomography device 1 as a medical diagnostic imaging device, in a perspective view. The magnetic resonance tomography device 1 includes a support device 2 that can be moved in a moving direction 3 and that supports an examination subject 4. The movable support device 2 including the patient 4 can be brought into different positions by a drive device 8 situated in the part of the device 1 that is stationary. A control device 9 controls the drive device 8. For generating magnetic resonance images of a fixable area 5 of the patient 4 to be imaged (an area of the upper body, in the example), a center of the area 5 to be imaged is to be positioned or centered by moving the support device 2 including the patient 4 in an imaging volume 6 within the examination space 7 of the device 1.

For prescribing the center of the area 5 to be imaged, for example, the device includes a pointer device 10 and a detection device 11. The detection device 11 is fashioned as a stereoscopic camera, which is arranged at a known distance from the stationary part of the device 1 and which is connected to the control device 9. The pointer device 10 is designed as a relatively long hand-held device having a tip 12 and that has at least two markers that can be optically acquired by the camera, as well as a press button 14.

After the patient 4 has been placed on the bearing device 2, a person carrying out the diagnosis prescribes the center of the area 5 to be imaged in the moving direction 3 by touching, for example with the tip 12, a corresponding point on the patient 4 with respect to the area 5 to be imaged, and thereby orients the pointer device 10 such that the pointer device 10 is directed toward the center of the area 5 to be imaged. The support device 2 thereby is situated in an initial position in which it is moved out of the examination space 7 as far as possible, for example, so that the patient 4 can simply lie down on the support device 2 or can be borne. For clarity, the figure merely shows a hand 15 of the person. After the pointer device 10 has been correspondingly oriented, the detection device 11, by operating the press button 14 for example, is initiated to detect the spatial position of the tip 12 as well as the orientation of the pointer device 10 and to inform the control device 9. Subsequently, the control device 9, in the moving direction 3, determines the center of the area 5 to be imaged and, on the basis of the known initial position of the bearing device 2, determines a moving path that is necessary for centering the center of the area 5 to be imaged in the imaging volume 6 of the device 1. Subsequent to a corresponding start signal, the control device 9 controls movement of the support device 2 along the aforementioned moving path.

In another embodiment, the press button 14 is not present at the pointer device 10, and the above-described function is assumed by a foot switch, for example, which is connected via an electrical cable to the control device 9 in a simple way and which is fashioned such that it can be operated with the foot of the person performing the diagnosis. Since the press button is foregone at the pointer device 10, the fashioning thereof as a hand-held device, which is free of a mechanical connection to other devices, is further facilitated.

In another embodiment, the pointer device 10 and detection device 11, which are based on an optical detection principle, are fashioned according to the aforementioned U.S. Pat. Nos. 5,828,770 and 5,923,417, for example. In other embodiments, non-optical detection principles can be utilized. The pointer device and the detection device must be magnetic resonance-compatible in all embodiments. This particularly means that the detection must operate reliably in the strong static basic magnetic field, in the rapidly switched magnetic gradient fields, and in the high-frequency transmission fields for exciting the magnetic resonance signals. Conversely, the pointer device and the detection device must not disturb the operation of the magnetic resonance tomography device.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical diagnostic apparatus comprising:
   an imaging device having an imaging volume a support device, adapted to receive an examination subject having a fixable area to be imaged, movable into and out of said imaging volume in at least one moving direction;
   a control device for controlling movement of said support device;
   a freely movable pointer for pointing to said fixable area to be imaged;
   a detection device for acquiring a spatial position of said pointer device, at least in said moving direction, and connected to said control device to control movement of said support device in at least said one moving direction to position said fixable area to be imaged within said imaging volume; and
   said pointer having no fixed connection to any of said imaging device, said support device, said control device or said detection device.

2. A medical diagnostic imaging apparatus as claimed in claim 1 wherein said imaging device has a stationary part, and wherein said detection device is disposed at a known distance from said stationary part.

3. A medical diagnostic imaging apparatus as claimed in claim 1 wherein said detection device detects an orientation of said pointer in addition to said spatial position of said pointer.

4. A medical diagnostic imaging apparatus as claimed in claim 1 wherein said pointer is a hand-held pointer.

5. A medical diagnostic imaging apparatus as claimed in claim 1 wherein said detection device optically detects said spatial position of said pointer.

6. A medical diagnostic imaging apparatus as claimed in claim 5 wherein said detection device optically detects an orientation of said pointer as well as optically detecting said spatial position.

7. A medical diagnostic imaging apparatus as claimed in claim 5 wherein said detection device is a stereoscopic camera.

8. A medical diagnostic imaging apparatus as claimed in claim 1 wherein said imaging device is a computed tomography device.

9. A medical diagnostic imaging apparatus as claimed in claim 1 wherein said imaging device is a magnetic resonance tomography device.

10. A medical diagnostic apparatus comprising:

an imaging device having an imaging volume a support device, adapted to receive an examination subject having a fixable area to be imaged, movable into and out of said imaging volume in at least one moving direction;

a control device for controlling movement of said support device;

a freely movable hand held pointer for pointing to said fixable area to be imaged; and a detection device for acquiring a spatial position of said pointer device, at least in said moving direction, and connected to said control device to control movement of said support device in at least said one moving direction to position said fixable area to be imaged within said imaging volume.

11. A medical diagnostic imaging apparatus as claimed in claim 10 wherein said imaging device has a stationary part, and wherein said detection device is disposed at a known distance from said stationary part.

12. A medical diagnostic imaging apparatus as claimed in claim 10 wherein said detection device detects an orientation of said pointer in addition to said spatial position of said pointer.

13. A medical diagnostic imaging apparatus as claimed in claim 10 wherein said detection device optically detects said spatial position of said pointer.

14. A medical diagnostic imaging apparatus as claimed in claim 13 wherein said detection device optically detects an orientation of said pointer as well as optically detecting said spatial position.

15. A medical diagnostic imaging apparatus as claimed in claim 13 wherein said detection device is a stereoscopic camera.

16. A medical diagnostic imaging apparatus as claimed in claim 10 wherein said imaging device is a computed tomography device.

17. A medical diagnostic imaging apparatus as claimed in claim 10 wherein said imaging device is a magnetic resonance tomography device.

* * * * *